United States Patent
Regnier et al.

(10) Patent No.: US 11,951,304 B2
(45) Date of Patent: Apr. 9, 2024

(54) IMPLANTABLE MEDICAL DEVICE WITH A NON-TRAUMATIC HELICAL ANCHORING SCREW

(71) Applicant: CAIRDAC S.A.S., Antony (FR)

(72) Inventors: Willy Regnier, Longjumeau (FR); An Nguyen-Dinh, La Riche (FR)

(73) Assignee: CAIRDAC S.A.S., Antony (FR)

(*) Notice: Subject to any disclaimer, the term of this patent is extended or adjusted under 35 U.S.C. 154(b) by 36 days.

(21) Appl. No.: 17/982,674

(22) Filed: Nov. 8, 2022

(65) Prior Publication Data

US 2023/0201578 A1 Jun. 29, 2023

(30) Foreign Application Priority Data

Dec. 29, 2021 (EP) .................................... 21315298

(51) Int. Cl.
  *A61N 1/05* (2006.01)
  *A61N 1/375* (2006.01)
(52) U.S. Cl.
  CPC ........... *A61N 1/059* (2013.01); *A61N 1/3756* (2013.01)
(58) Field of Classification Search
  CPC ...... A61N 1/0558; A61N 1/057; A61N 1/059; A61N 1/37518
  See application file for complete search history.

(56) References Cited

U.S. PATENT DOCUMENTS

| | | | |
|---|---|---|---|
| 4,311,153 A | 1/1982 | Smits | |
| 11,197,997 B2 * | 12/2021 | Regnier | A61N 1/37518 |
| 2004/0133243 A1 * | 7/2004 | Santamore | A61N 1/056 607/5 |
| 2009/0259212 A1 * | 10/2009 | Sabbah | A61M 5/46 604/117 |
| 2011/0307043 A1 * | 12/2011 | Ollivier | A61N 1/37518 607/127 |
| 2017/0209688 A1 * | 7/2017 | Drake | A61N 1/057 |
| 2019/0001119 A1 * | 1/2019 | Schmidt | A61B 6/12 |
| 2020/0147365 A1 * | 5/2020 | Marshall | A61N 1/362 |
| 2020/0197705 A1 | 6/2020 | Drake | |
| 2020/0289835 A1 | 9/2020 | Eby | |
| 2020/0306522 A1 * | 10/2020 | Chen | A61N 1/059 |

* cited by examiner

*Primary Examiner* — Eric D. Bertram
(74) *Attorney, Agent, or Firm* — CRGO Global; Steven M. Greenberg

(57) ABSTRACT

The device, such as an autonomous cardiac implant of the leadless capsule type, has a device body with a means for its anchoring to a patient's organ wall. The anchoring means includes a screw with a helix wire wound into a plurality of non-contiguous turns, the screw having a clamped end integral with the front face of the device body and a free end with a beveled end defined by at least one oblique surface. The normal to the oblique surface of the beveled end is directed away from the front face, in such a way that the oblique surface is directed towards the patient's organ wall. The normal to the oblique surface forms an angle between 30° and 60° with respect to the helix axis, and the screw is elastically deformable in axial compression, with a stiffness coefficient of at most 5 N/mm.

10 Claims, 4 Drawing Sheets

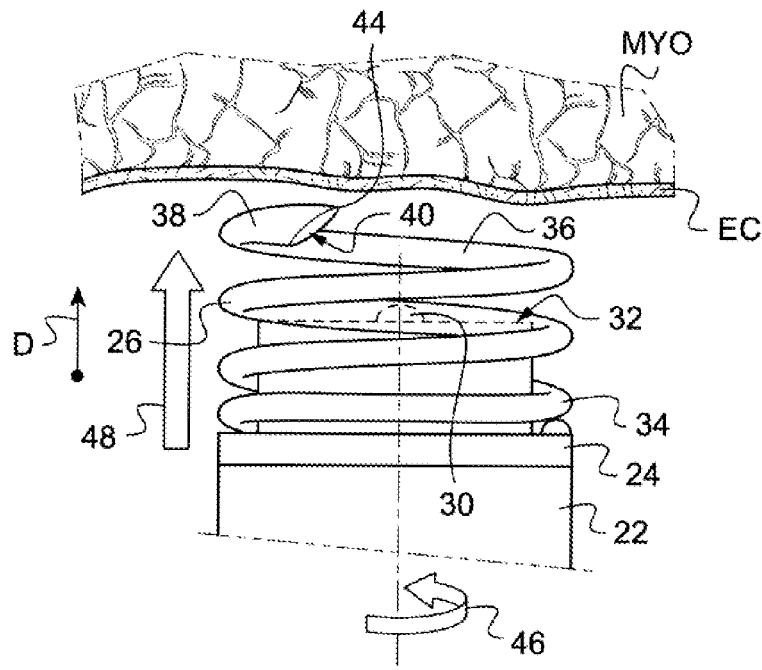
Fig.3
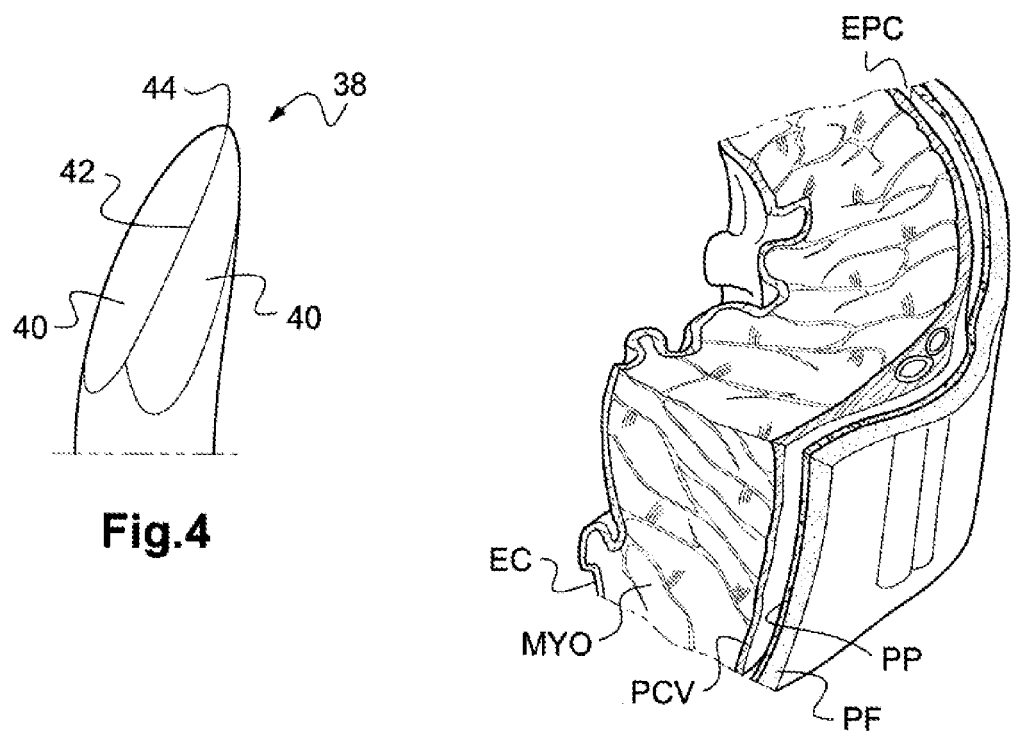
Fig.4
Fig.5

IMPLANTABLE MEDICAL DEVICE WITH A NON-TRAUMATIC HELICAL ANCHORING SCREW

CROSS REFERENCE TO RELATED APPLICATIONS

This application claims priority under 35 U.S.C. § 119(a) to COUNTRY patent application 21315298.6 filed on 29 Dec. 2021, the entire teachings of which are incorporated herein by reference.

BACKGROUND OF THE INVENTION

Field of the Invention

The present invention relates to implanted medical devices, in particular those which are intended to be implanted into a heart cavity, and more particularly to autonomous implantable devices of the "leadless capsule" type, which are implantable devices having no physical connection (lead) with a remote device, and which are anchored to an implantation site with a helical screw.

Description of the Related Art

In the art of cardiac implantable devices, an implanted capsule continuously monitors the patient's rhythm and, if necessary, issues to the heart electrical pulses for pacing, resynchronization and/or defibrillation in case of rhythm disorders detected by the capsule. The capsule includes various electronic circuits, sensors, etc., as well as wireless communication transmission/reception means for the remote exchange of data, the whole being integrated in a very small size body able to be implanted at sites of difficult access or leaving little available space, such as the ventricle apex, the inner wall of the atrium. In particular, implementing an atrial capsule offers the significant advantage of allowing a pacing of the "dual chamber" type, combining a ventricular capsule with an atrial capsule, both provided with mutual communication means. The atrial capsule detects the atrial depolarizations of the sinus rhythm, and the ventricular capsule, as well as possibly the atrial capsule, issue(s) as needed to the ventricle and/or to the atrium pacing pulses sequenced in such a way as to accurately control the atrioventricular pacing delay.

Generally, an implantable capsule is provided at its distal end with an anchoring member adapted to enter the tissues of a body wall. In the case of an endocavitary capsule, the capsule is fixed to the inner wall of a ventricular or atrial chamber. Several types of anchoring devices exist, often with elastically deformable tines extending into the mass of the myocardium, but also anchoring means implementing a protruding helical screw axially extending the capsule body and adapted to enter the heart tissue at the implantation site by being screwed thereinto.

The "delivery" of the capsule, that is to say, its positioning to the implantation site, consists in mounting the capsule at the end of a guide-catheter of an implantation accessory, then to make it move along the peripheral venous network and to drive it up to the chosen site, for example the apex of the right ventricular chamber. Once the implantation site reached, by means of the guide-catheter, the practitioner imparts to the capsule a combined movement of axial translation (to make the capsule move forward then to exert a pressure against the heart wall) and rotation of the capsule about itself (to screw the anchoring member into the heart wall thickness). Once the capsule firmly anchored, the practitioner proceeds to the "release" of the capsule, i.e. its separation from the implantation accessory, so that the capsule then becomes fully autonomous.

Published international application WO 2002/064172 A1 by Cairdac, corresponding to U.S. Pat. No. 11,197,997 B2 describes a capsule provided with a helical anchoring screw, and further provided with a torque limitation system making it possible to disengage the capsule body from the anchoring screw when the reaction torque exerted by the anchoring screw exceeds a predetermined threshold, in such a way as not to exceed a limit value known as "coring torque" beyond which the anchoring screw would risk to locally tear the tissues under the effect of rotation of the screw without forward move of the latter, until causing a laceration of the tissues and, in the extreme, a piercing of the wall with a risk of tamponade. Further, United States Patent Application Publication No. 2020/289835 A1 by Eby et al. discloses another type of anchoring member including two coaxial screws of different lengths, with an external screw and an internal screw, both with a pointed and piercing beveled end.

As will be explained in detail hereinafter, this risk of damaging the tissues is particularly high in case of implantation in a thin wall such as that of the atrium, in particular in the region of the right atrial appendage (RAA), considering the very low thickness, typically of the order of 0.5 to 2 mm, according to the location. The difficulty is increased by the fact that the RAA region contains many folds and it is not possible to predict the exact thickness at the implantation site before the screwing and, moreover, in case of piercing of the heart wall, it is not possible to detect a bleeding, the blood effusion occurring inside the pericardial sac (hemorrhagic tamponade). Moreover, due to these folds, it is not possible to determine exactly the angle that the capsule will form with the myocardium at the time of contact with the heart wall. If the direction is oblique, the risk of piercing is lower, but the risk of a wrong detection threshold is higher, and vice versa.

In any case, given the reduced wall thickness, the fixing length of the helix (length of the screw beyond the front flat side of the capsule that supports the sensing/pacing electrode) will necessarily be lower than 1.5 mm, which is a reduced length making it difficult to obtain a reliable and lasting anchoring of the device to the atrium wall.

BRIEF SUMMARY OF THE INVENTION

The invention more particularly relates to the anchoring of the capsule, or more generally the medical device, to the chosen implantation site. The present invention has for object to propose an implantable medical device provided with a screw anchoring allowing a mechanically secure and clinically safe fixing to a thin wall, by making sure not to pass through the thin wall of the organ with helix—in particular, in case of implantation in the atrium, to protect the pericardial space and to prevent any bleeding.

To solve these problems and reach the objects exposed hereinabove, the invention proposes for that purpose an implantable medical device including a device body with a front face at its distal end, and a means for anchoring the medical device to the heart wall. The anchoring means includes a screw with a helix wire wound into a plurality of non-contiguous turns, the screw having a clamped end integral with the front face of the device body, and a free end with a beveled end defined by at least one oblique surface. The normal to the oblique surface of the beveled end is directed away from the front face of the device body, in such a way that the oblique surface is directed towards the heart wall, the normal to the oblique surface forms an angle between 30˗∞ and 60˗∞ with respect to the helix axis, and the screw is elastically deformable in axial compression.

Characteristically of the invention, (i) the screw is a non-piercing screw devoid of tip or cutting edge, (ii) the oblique surface has at its end a rounded edge adapted to slide over the visceral pericardium without piercing it, (iii) the length of the active turns of the screw is lower than 1.5 mm, and (iv) the stiffness coefficient K of the screw in axial compression is at most 5 N/mm, so that, during an implantation in an atrial wall, the screw, after having reached the visceral pericardium, produces a crushing of the myocardium without piercing the visceral pericardium whereby avoiding any blood effusion in the pericardial space.

According to various advantageous subsidiary features:
the oblique surface is a flat surface;
the radius of curvature of the rounded edge of the oblique surface is such that the rounded diameter:wire diameter ratio is at most 1:5;
the radius of curvature of this rounded edge is a radius progressively decreasing from a maximum value at the most distal end of the oblique surface edge;
the beveled end has two oblique surfaces mutually arranged as a dihedron, and the normal to each oblique surface is directed away from the front face of the device body, in such a way that the two oblique surfaces as well as an edge of the dihedron are directed towards the patient's organ wall;
the stiffness coefficient K of the screw in axial compression is at most 1 N/mm;
the device further includes a disengageable coupling arranged in such a way as, when an external axial rotational stress is applied to the device body in a screwing direction of the screw, to allow a relative axial rotation between the device body and the anchoring means as soon as a reaction torque exerted by the screw in the patient's organ wall exceeds a predetermined threshold torque;
at least over the extent of a terminal half-turn of the helix, the bending stiffness of the helix wire is a non-constant stiffness, lower in a region located near the free end of the helix wire;
the helix wire of the screw has at least one of the following features: wire diameter: 0.2 to 1 mm; external helix diameter: lower than 26 Fr (8.67 mm); number of turns: 1 to 5 turns; no-load winding pitch: 1 mm, constant or variable.

The device according to the invention may in particular be an autonomous cardiac implant of the leadless capsule type, wherein the device body receives an electronic unit and an energy harvesting module with an energy storage means for powering the electronic unit, and wherein the front face of the device body carries a cardiac sensing/pacing electrode adapted to come into contact with the patient's organ wall after anchoring of the device.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein:

FIG. 3 shows more precisely the distal end of a leadless capsule provided with an anchoring screw according to the state of the art, with the screw end approaching the wall of the implantation site.

FIG. 4 is a detail view of the beveled end of the anchoring screw of FIG. 3.

FIG. 5 is a cross-sectional view of a heart wall, in particular at the atrium, showing in detail the different tissues the wall is formed of.

DETAILED DESCRIPTION OF THE INVENTION

An exemplary embodiment of the device of the invention will now be described, in an application to an autonomous implantable capsule intended to be implanted into a heart cavity.

As indicated hereinabove, this particular application is given only as an example of embodiment and does not limit the invention, whose teachings can be applied to many other types of implantable devices.

Figure 1:
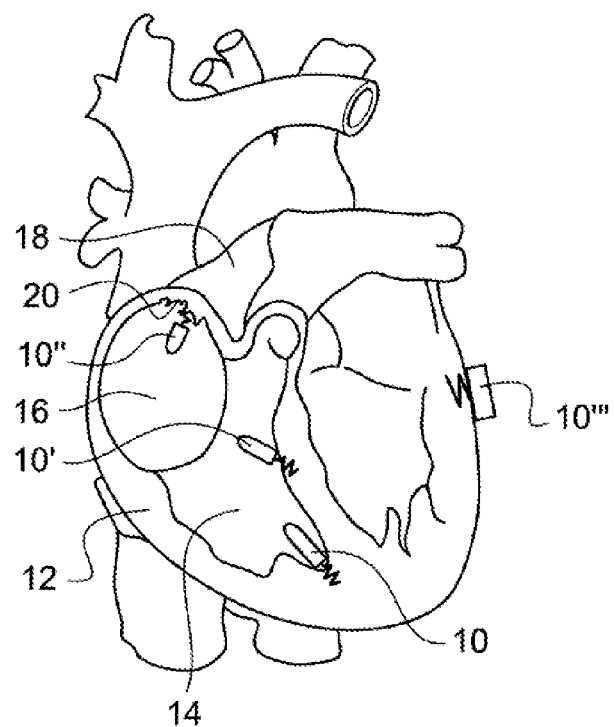
FIG. 1 illustrates medical devices of the leadless capsule type in their environment, with various examples of implantation sites in, on or near a patient's heart.

FIG. 1 shows various possibilities of implantation sites for an implantable medical device of the leadless capsule type, in an application to cardiac pacing. Thus, the capsule denoted 10 is implanted at the apex of the right ventricle 14 of the myocardium 12. The capsule may also be implanted on the interventricular septum, as in 10', or also on a right atrial wall 16, as in 10". The device may also be an epicardial capsule placed on an external region of the myocardium, as illustrated in 10'".

Hereinafter will be described in more detail, with reference in particular to FIG. 5, the specific case of implantation in the region of the right atrial appendage 18, where the heart wall inside the atrium 16 has a more reduced thickness, as well as a number of folds and trabeculations 20; this region has for advantage not to be in the continuation of the superior vena cava and the tricuspid valve, so that the presence of a capsule at this place won't impede access to the other areas of the atrial or ventricular chambers, in particular to accede to the bottom of the ventricle if it is desired to implant a capsule into the apex region or to explant it therefrom.

In any case, the leadless capsule is fixed to the heart wall by means of a protruding anchoring system entering the heart tissue in order to hold it in place at the implantation site. Various systems can be used, the invention relating more particularly to the capsules provided with a helical screw anchoring member.

Figure 2:
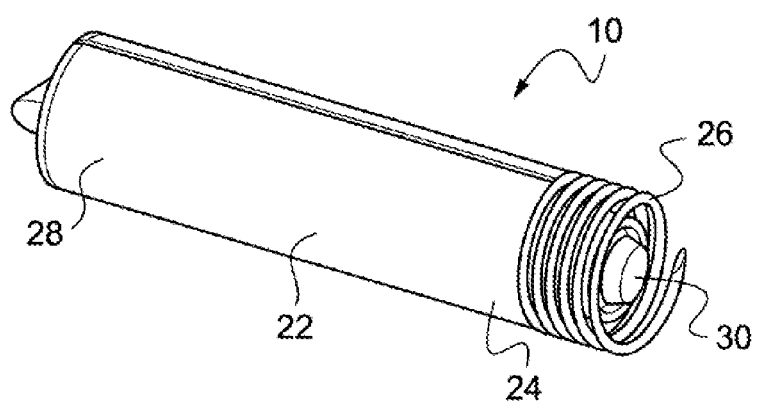
FIG. 2 is an overall external view of a leadless capsule, showing in particular the anchoring screw and the pacing electrode at its distal end.

As illustrated in FIG. 2, a capsule provided with such a member has generally the shape of a tubular body 22 enclosing the various electronic and power supply circuits of the capsule. The typical size of the known capsules is a diameter of the order of 6 mm for a length of about 25 to 40 mm. The tubular body 22 has, at its front (distal) end 24, a cylindrical helical screw 26 intended to hold the capsule in place at the implantation site. The opposite (proximal) rear end 28 is a free end, which is only provided with means (not shown) for the temporary connection to a guide catheter or another implantation accessory usable for implantation or explantation of the capsule, which is then detached from the latter.

To ensure the sensing/pacing functions, an electrode 30 is arranged on the front face of the capsule; once the capsule anchored at the implantation site, the electrode 30 is in contact with the heart tissue, hence making it possible to collect the cardiac depolarization potential and/or to apply pacing pulses.

FIG. 3 shows more precisely the distal end of the capsule with the helical screw 26 approaching the heart wall, including the myocardium MYO and the endocardium EC.

At the time of implantation, the front face 32 of the capsule body 22, which carries the electrode 30, is turned towards the endocardium wall. The helical screw 26 includes, on the proximal side, inactive turns 34 integral with the body 22 of the capsule, and, on the other side, active turns 36 ended by a beveled free end 38.

Such a capsule is for example described by abovementioned WO 2002/064172 A1 (U.S. Pat. No. 11,197,997 B2) or US 2020/289835 A1.

FIG. 4 illustrates more precisely the beveled tip 38, which is a piercing tip having one or several oblique surfaces 40 making it possible to create a cutting edge 42 with a piercing tip 44 at the most distal end of the helical screw. As can be seen in FIG. 3, the piercing end 44 is directed towards the heart wall, with the oblique surfaces 40 turned in the proximal direction (the distal direction being denoted by the reference D in FIG. 3).

This configuration with the tip turned towards the wall (that is to say in the distal direction D) facilitates the piercing of the endocardium EC then the penetration into the myocardium MYO in the different configurations liable to be met, even in case of inclination between the capsule axis and the normal to the wall when it comes into contact with the latter. Once the tip 44 in contact with the endocardium EC, the combined movement of rotation 46 and translation 48 (axial thrust) exerted by the practitioner via the guidecatheter ensures the piercing of the endocardium EC and the penetration of the screw into the myocardium MYO over the length of the active turns 36, which is of the order of 1.5 mm or more for a fixing to the ventricular chamber. The front face 32 carrying the electrode 30 is then in contact with the heart wall, allowing the electrode to ensure its sensing/pacing functions.

The known anchorage screw configuration described above with reference to FIGS. 3 and 4 is however ill-suited for a fixing to the atrium, as care must be taken not to pierce the wall.

FIG. 5 illustrates the various tissues constituting the heart wall of the atrium, in particular at the right atrial appendage (RAA): the wall includes, from the inside to the outside, the endocardium EC, the myocardium MYO, the visceral pericardium PCV, the pericardial space EPC, the parietal pericardium PP and the fibrous pericardium PF.

The total thickness of the wall is included between 0.5 and 2 mm, hence a far lower value than that of the ventricle, whether it is at the apex or the septum. Moreover, the visceral pericardium PCV is a very thin wall, of about 0.2 mm thick, which is passed through in places by coronary blood vessels. If it is desired to implant into such a wall a capsule provided with a screw-based anchoring member, the visceral pericardium PCV must absolutely not be passed through with the screw helix, in order to avoid any piercing that would create a risk of hemorrhagic tamponade with blood effusion in the pericardial space EPC. However, it is necessary to penetrate sufficiently into the myocardium MYO to guarantee a good fixing of the capsule to the heart wall.

To solve this problem, the invention proposes a new configuration of anchoring screw, illustrated in FIGS. 6 to 11.

Figure 6:
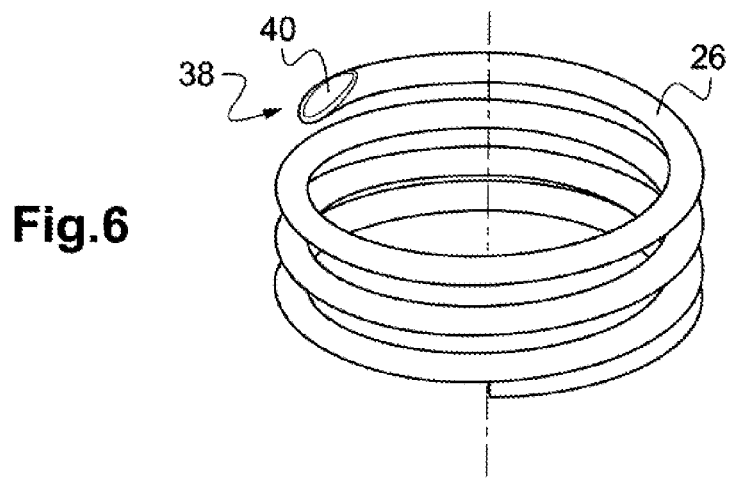
FIG. 6 is a perspective view of an anchoring screw according to the present invention.

As illustrated in FIG. 6, the helical screw 26 is ended by a free beveled end 38 defined by at least one oblique surface 40.

The oblique surface 40 may be a flat surface. It may also be a curved surface, for example a conical surface such as the surface of a cone of revolution or an oblique cone whose region close to the apex would have been blunted not to be traumatic.

Figure 10:
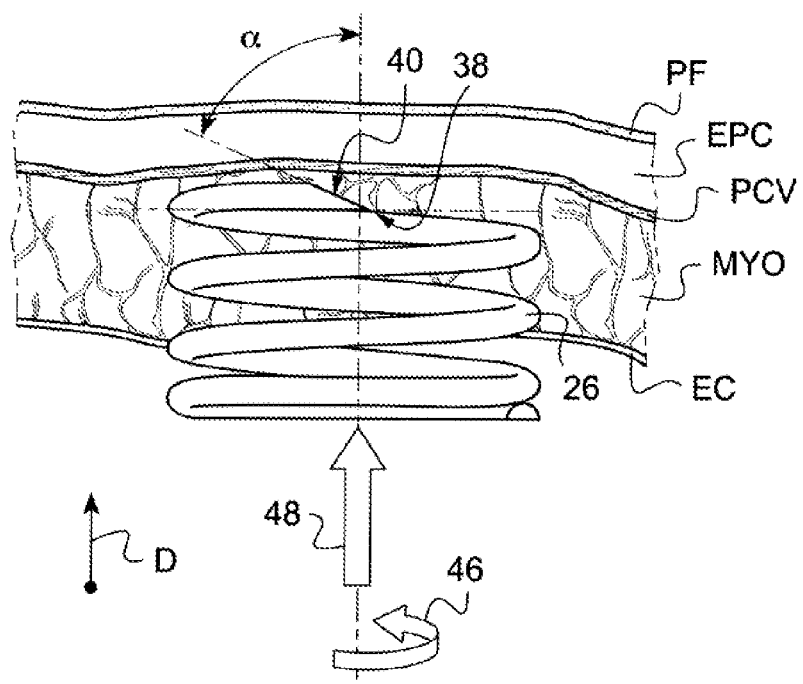
FIG. 10 shows the distal end of an anchoring screw according to the invention, during the penetration of the heart wall at the implantation site.

Characteristically of the invention, the oblique surface 40 defining the bevel of the end 38 is turned towards the wall, that is to say in the distal direction D (cf. FIG. 10). In other words, the normal to the oblique surface 40 is directed away from the front face of the device body, in such a way that this oblique surface 40 is turned towards the organ wall—unlike the anchoring screws of the state of the art, in which the oblique surface of the bevel is directed away from the wall (as illustrated in FIG. 3).

The normal to the oblique surface oblique forms an angle (cf. FIG. 10) typically between 30¬∞ and 60¬∞ with respect to the helix axis.

Another feature of the anchoring helical screw according to the invention is that it is elastically deformable in axial compression, with a stiffness coefficient of at most 5 N/mm.

The helix wire may in particular have the following characteristics (which are in themselves non-limiting to the invention):
  right winding;
  biocompatible material such as stainless steel, titanium, nitinol, etc., advantageously with a coating providing a surface state forming micro-reliefs (titanium nitride coating) or a porosity (by chemical etching) that promote adhesion of the screw to fibrotic tissues after implantation;
  wire diameter: 0.2 to 1 mm;
  external diameter of the helix: lower than 26 Fr (8.67 mm);
  number of active turns: 1 to 5 turns;
  no-load winding pitch: 1 mm (the pitch can potentially be a variable pitch);

length of the active turns in the axial direction: lower than 1.5 mm.

Figure 7:
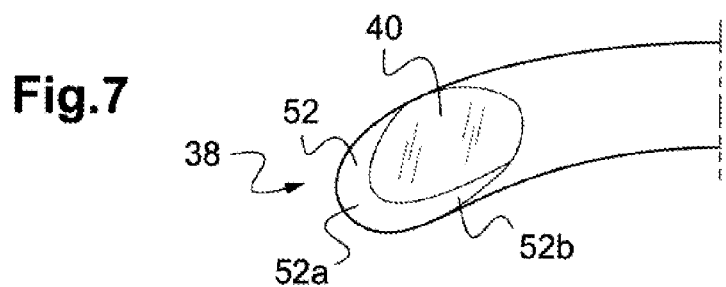
FIG. 7 is a detail view of the distal end of the anchoring screw of FIG. 6.

The beveled end 38 is made by a machining making it possible to shape the oblique surface 40. Advantageously, as illustrated in FIG. 7, a round 52 is made over the periphery of the oblique surface 40, by traditional machining or by laser shooting. The rounded edge 52 allows eliminating the cutting edge (which existed with the helical screws of the prior art as illustrated in FIGS. 3 and 4) and making the geometry of the helical screw end atraumatic. The piercing of the visceral pericardium is hence prevented by eliminating any tip or cutting edge at the end of the helix. Advantageously, the round formed at the end of the helix is a variable round, with a radius value decreasing progressively from the distal end 52a to the less distal region 52b. The round diameter at the distal end 52a is for example of 0.1 mm, generally a round diameter lower than ⅕ of the wire diameter.

Figure 8:
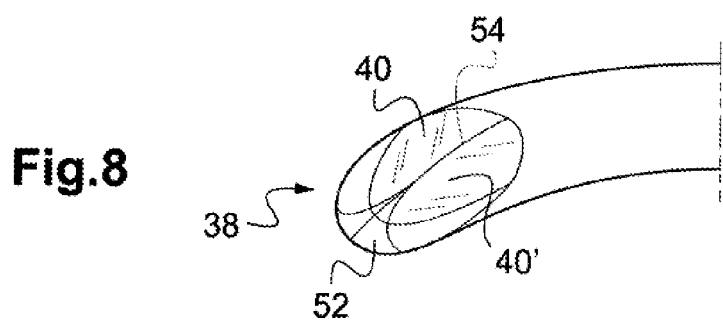
FIG. 8 illustrates an alternative of FIG. 7.

FIG. 8 illustrates an alternative of FIG. 7, in which the beveled end 38 includes two oblique surfaces 40, 40' forming at their intersection an edge 54, also rounded in such a way as not to be sharp.

Figure 9:
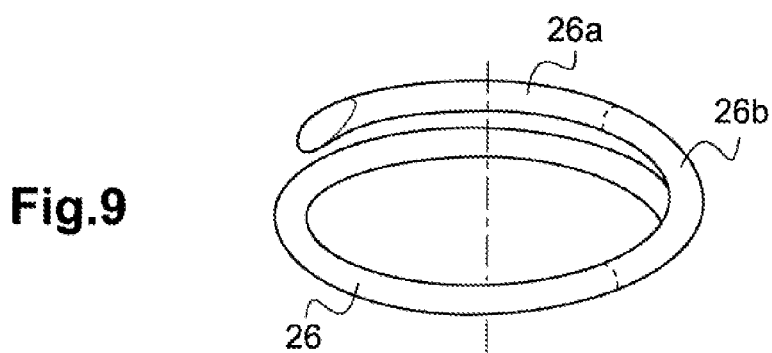
FIG. 9 illustrates a particular embodiment in which the anchoring screw has a bending stiffness that is not constant near the distal end of the helix.

FIG. 9 illustrates a particular embodiment in which the bending stiffness of the helix wire (wire stiffness on the helix development, to be distinguished from the axial compression stiffness mentioned above) is a variable stiffness. For that purpose, the wire is consisted of one or several areas having different bending stiffnesses, for example a juxtaposition of wire portions 26a, 26b of different respective stiffnesses K1 and K2, or with a wire of variable diameter, or also by a specific mode of manufacturing (thermal annealing differentiated according to the regions of the wire). Non-limiting stiffness values are for example K1=0.3 N/mm, K2=0.6 N/mm, or K varying from 0.1 to 1 N/mm, over a length of the terminal half-turn of the helix.

The way the implantation of the capsule is performed by means of the just-described screw according to the invention will now be explained, with reference to FIGS. 10 and 11.

With this screw, unlike the solutions of the prior art, the end of the helical screw is designed in such a way as not to pierce the heart wall.

The matter is essentially, under the effect of the dual movement of rotation 46 and axial compression 48 imparted by the operator, to make the helix enter the myocardium without cutting the latter (which has very little resistance), then to make the helix end slide on the visceral pericardium PCV without piercing it, thus creating a non-piercing fixing mode. The inclined oblique surface 40 will only push away the visceral pericardium by sliding thereon, without piercing it.

Figure 11:
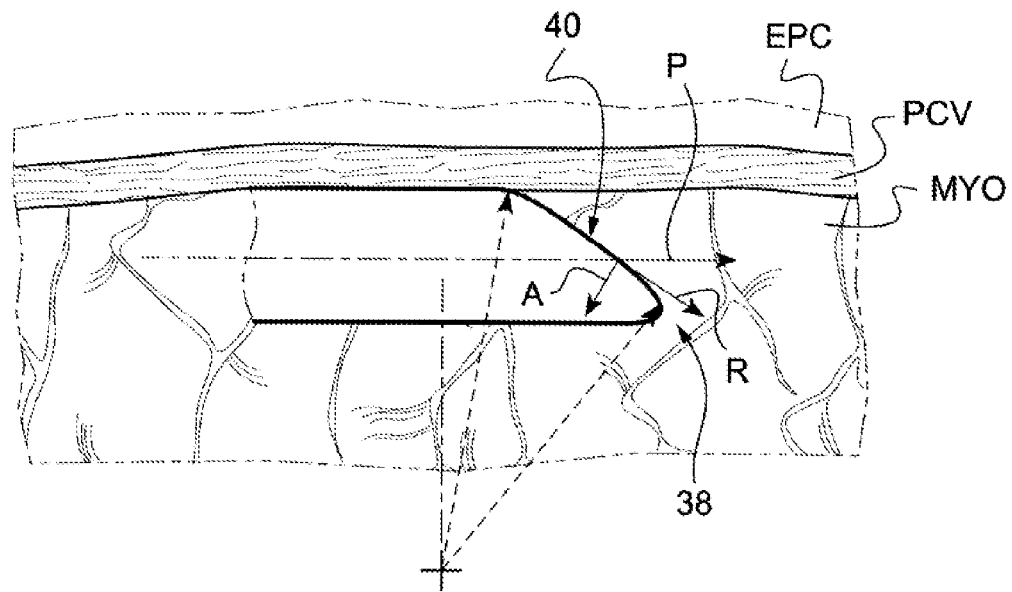
FIG. 11 is an enlarged schematic view of the beveled end of the anchoring screw according to the invention, explaining the different forces exerted at this end, as well as the resultant thereof.

FIG. 11 shows the distribution of the efforts and stresses at the helix end.

In an initial phase, when the helix has entered the myocardium and has not yet reached the visceral pericardium, the axial pressing force on the heart tissue is lower than the axial compression stiffness K of the helix wire. The pressing force A of the oblique surface 40, combined with the radial thrust P produced by the rotation of the screw, produces at the bevel end 38 a resultant R that is insufficient to pass through the visceral pericardium PCV and to risk damaging the latter.

Once the screw has reached the visceral pericardium PCV, the thrust force becomes higher than the stiffness K of the helix wire, due to the fact that the resistance of the visceral pericardium PCV is higher than that of the myocardium MYO. The screw helix will then be compressed, by crushing the myocardium without piercing the visceral pericardium.

Moreover, if a helix wire having a variable bending stiffness is provided, as exposed hereinabove with reference to FIG. 9, once having reached the visceral pericardium, the terminal part of the screw will be deformed according to a non-helical geometry due to the greater flexibility (lower bending stiffness) of its end.

Advantageously, the implant is provided with a torque limiter, made for example according to the teachings of above-mentioned WO 2002/064172 A1 (U.S. Pat. No. 11,197,997 B2), which will allow disengaging the anchoring member from the implant body when the reaction torque exerted by the screw in the organ wall exceeds a predetermined threshold torque, thus avoiding any laceration of the tissues.

The just-described particular helical screw configuration makes it possible to have a "smart", adaptive anchoring helix: in the fragile but more resistant tissue of the pericardium, the risk of piercing is strongly reduced, by keeping a capacity of sliding in the softer tissue of the myocardium. The fixing length of the helix is thus maximized over the almost-totality of the atrium wall thickness, although the latter is thinner and less fragile than in the case of a ventricular implantation. Of note, the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes", and/or "including," when used in this specification, specify the presence of stated features, integers, steps, operations, elements, and/or components, but do not preclude the presence or addition of one or more other features, integers, steps, operations, elements, components, and/or groups thereof.

As well, the corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Having thus described the invention of the present application in detail and by reference to embodiments thereof, it will be apparent that modifications and variations are possible without departing from the scope of the invention defined in the appended claims as follows:

1. An implantable medical device adapted to be implanted into a thin heart wall of a patient, in particular into an atrial wall comprising successively an endocardium, a myocardium and a visceral pericardium, the device comprising:
   a device body with a front face at its distal end; and
   a means for anchoring the medical device to said heart wall,
   wherein the means for anchoring includes a screw with a helix wire wound into a plurality of non-contiguous turns, the screw having a clamped end integral with the front face of the device body and a free end comprising a beveled end defined by at least one oblique surface, wherein:
the normal to the oblique surface of the beveled end is directed away from the front face of the device body, in such a way that the oblique surface is directed towards the heart wall,
the normal to the oblique surface forms an angle between 30° and 60° with respect to the helix axis, and
the screw is elastically deformable in axial compression, wherein the screw is a non-piercing screw devoid of tip or cutting edge, and wherein:
the oblique surface has at its end a rounded edge adapted to slide over the visceral pericardium without piercing it,
the length of the active turns of the screw is lower than 1.5 mm, and the stiffness coefficient K of the screw in axial compression is at most 5 N/mm, so that, during an implantation in an atrial wall, the screw, after having reached the visceral pericardium, produces a crushing of the myocardium without piercing the visceral pericardium,
whereby avoiding any blood effusion in the pericardial space.

2. The device of claim 1, wherein the oblique surface is a flat surface.

3. The device of claim 1, wherein the radius of curvature of the rounded edge of the oblique surface is such that the rounded diameter: wire diameter ratio is at most 1:5.

4. The device of claim 3, wherein the radius of curvature of this rounded edge is a radius progressively decreasing from a maximum value at the most distal end of the oblique surface edge.

5. The device of claim 1, wherein the beveled end has two oblique surfaces mutually arranged as a dihedron, and wherein the normal to each oblique surface is directed away form the front face of the device body, in such a way that the two oblique surfaces as well as an edge of the dihedron are directed towards the patient's organ wall.

6. The device of claim 1, wherein the stiffness coefficient K of the screw in axial compression is at most 1 N/mm.

7. The device of claim 1, further comprises a disengageable coupling arranged in such a way as, when an external axial rotational stress is applied to the device body in a screwing direction of the screw, to allow a relative axial rotation between the device body and the means for anchoring as soon as a reaction torque exerted by the screw in the patient's organ wall exceeds a predetermined threshold torque.

8. The device of claim 1, wherein, at least over the extent of a terminal half-turn of the helix, the bending stiffness of the helix wire is a non-constant stiffness, lower in a region located near the free end of the helix.

9. The device of claim 1, wherein the helix wire of the screw has only one of the following characteristics:
wire diameter: 0.2 to 1 mm;
external diameter of the helix: lower than 26 Fr (8.67 mm);
number of turns: 1 to 5 turns;
no-load winding pitch: 1 mm, constant or variable.

10. The device of claim 1, wherein:
the medical device is an autonomous cardiac implant of the leadless capsule type,
the device body receives an electronic unit and an energy harvesting module with an energy storage means for powering the electronic unit, and
the front face of the device body carries a cardiac sensing/pacing electrode adapted to come into contact with the patient's organ wall after anchoring of the device.

* * * * *